United States Patent
Cully et al.

(10) Patent No.: US 10,806,892 B2
(45) Date of Patent: Oct. 20, 2020

(54) DECONSTRUCTABLE ENDOLUMINAL DEVICES AND RELATED SYSTEMS AND METHODS

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Brian C. Martonik, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 623 days.

(21) Appl. No.: 15/374,495

(22) Filed: Dec. 9, 2016

(65) Prior Publication Data

US 2017/0087331 A1    Mar. 30, 2017

Related U.S. Application Data

(62) Division of application No. 14/186,634, filed on Feb. 21, 2014, now Pat. No. 9,539,411.

(60) Provisional application No. 61/779,038, filed on Mar. 13, 2013.

(51) Int. Cl.
*A61M 25/00* (2006.01)
*A61M 25/06* (2006.01)

(52) U.S. Cl.
CPC ...... *A61M 25/005* (2013.01); *A61M 25/0045* (2013.01); *A61M 25/0662* (2013.01); *A61M 25/0668* (2013.01)

(58) Field of Classification Search
CPC ............ A61M 25/0012; A61M 25/005; A61M 25/0051; A61M 25/0074; A61M 25/0668; A61M 2025/0034; A61M 2025/0063; A61M 2025/0074; A61M 2025/0079; A61M 2025/0118
See application file for complete search history.

(56) References Cited

U.S. PATENT DOCUMENTS

| | | | |
|---|---|---|---|
| 4,569,347 A * | 2/1986 | Frisbie | A61M 29/02 604/164.05 |
| 5,066,285 A | 11/1991 | Hillstead | |
| 5,209,734 A | 5/1993 | Hurley et al. | |
| 5,234,425 A | 8/1993 | Fogarty | |
| 5,246,452 A * | 9/1993 | Sinnott | A61F 2/06 623/1.23 |
| 5,304,140 A | 4/1994 | Kugo | |
| 5,395,349 A | 3/1995 | Quiachon | |
| 5,405,378 A | 4/1995 | Strecker | |
| 5,431,676 A | 7/1995 | Dubrul et al. | |
| 5,752,937 A | 5/1998 | Otten et al. | |
| 5,961,499 A | 10/1999 | Bonutti | |
| 6,159,198 A * | 12/2000 | Gardeski | A61M 25/0668 604/161 |
| 6,224,627 B1 | 5/2001 | Armstrong | |

(Continued)

FOREIGN PATENT DOCUMENTS

WO    WO-2012147604    11/2012

OTHER PUBLICATIONS

International Search Report for PCT/US2014/018437 dated May 26, 2014, corresponding to U.S. Appl. No. 14/186,634; 5 pages.

*Primary Examiner* — Laura A Bouchelle

(57) ABSTRACT

An endoluminal device comprises a tubular member and a reinforcement member that is separable from, or together with, a wall of the tubular member, and removable in-situ.

18 Claims, 6 Drawing Sheets

(56) References Cited

U.S. PATENT DOCUMENTS

| | | | |
|---|---|---|---|
| 6,254,628 B1 | 7/2001 | Wallace et al. | |
| 6,315,792 B1 | 11/2001 | Armstrong et al. | |
| 6,358,238 B1* | 3/2002 | Sherry | A61M 25/0023 604/524 |
| 6,371,953 B1 | 4/2002 | Beyar | |
| 6,398,758 B1 | 6/2002 | Jacobsen | |
| 6,551,350 B1 | 4/2003 | Thornton et al. | |
| 6,827,731 B2 | 12/2004 | Armstrong et al. | |
| 6,837,870 B2 | 1/2005 | Duchamp | |
| 6,939,327 B2 | 9/2005 | Hall | |
| 7,011,648 B2* | 3/2006 | Breskot | A61M 25/0668 604/161 |
| 7,553,387 B2 | 6/2009 | Leeflang et al. | |
| 7,637,902 B2 | 12/2009 | Eversull et al. | |
| 8,500,775 B2 | 8/2013 | Chomas | |
| 8,845,712 B2* | 9/2014 | Irwin | A61F 2/966 623/1.11 |
| 9,539,411 B2* | 1/2017 | Cully | A61M 25/0045 |
| 2003/0212373 A1* | 11/2003 | Hall | A61M 25/0668 604/263 |
| 2003/0233115 A1 | 12/2003 | Eversull | |
| 2005/0085542 A1 | 4/2005 | Arduini | |
| 2005/0085842 A1* | 4/2005 | Eversull | A61F 2/966 606/191 |
| 2005/0182387 A1* | 8/2005 | Webler | A61M 25/0668 604/527 |
| 2006/0052750 A1 | 3/2006 | Lenker et al. | |
| 2007/0049946 A1* | 3/2007 | Mackley | A61M 25/0668 606/108 |
| 2007/0060880 A1 | 3/2007 | Gregorich et al. | |
| 2007/0225815 A1 | 9/2007 | Keith | |
| 2007/0276354 A1 | 11/2007 | Osborne | |
| 2008/0033396 A1 | 2/2008 | Danek et al. | |
| 2008/0048011 A1* | 2/2008 | Weller | A61M 25/0009 229/87.05 |
| 2009/0043285 A1 | 2/2009 | Stehr | |
| 2010/0030321 A1* | 2/2010 | Mach | A61F 2/07 623/1.18 |
| 2010/0262231 A1 | 10/2010 | Tuval | |
| 2010/0268243 A1 | 10/2010 | Parker | |
| 2011/0137399 A1 | 6/2011 | Chomas et al. | |
| 2014/0046134 A1 | 2/2014 | Kikuchi | |

* cited by examiner

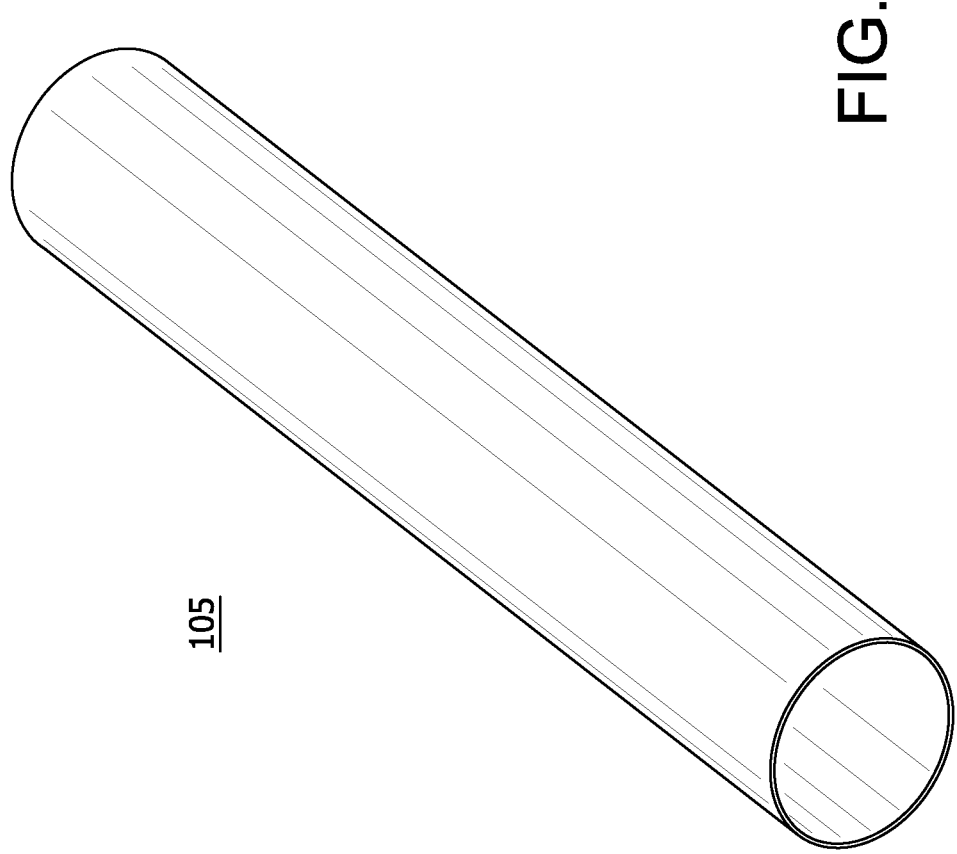

A # DECONSTRUCTABLE ENDOLUMINAL DEVICES AND RELATED SYSTEMS AND METHODS

CROSS-REFERENCE TO RELATED APPLICATIONS

This application is a divisional of U.S. application Ser. No. 14/186,634, filed Feb. 21, 2014, which claims priority to U.S. Provisional Application No. 61/779,038, filed Mar. 13, 2013, both of which are incorporated by reference herein in their entireties for all purposes.

BACKGROUND

Field

The disclosure relates to atraumatic removal of endoluminal devices. More particularly, the disclosure relates to endoluminal devices which are deconstructable in-situ to facilitate removal therefrom.

Discussion of the Related Art

Endoluminal devices are routinely used by clinicians in connection with a wide variety of vascular procedures. Due to the duration and/or the nature of a given procedure, tissue ingrowth, and/or dehydration, an endoluminal device may be difficult to remove upon completion of the procedure. For example, an introducer inserted through an iliac artery may become attached or stuck to the vascular wall, such that attempting to remove the introducer could cause damage to the artery. Thus, it remains desirable to provide improved atraumatic removal of endoluminal devices. The present disclosure addresses this need.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

FIG. 1 illustrates a tubular member in accordance with the present disclosure;

DETAILED DESCRIPTION OF THE ILLUSTRATIVE EMBODIMENTS

Figure 2B:
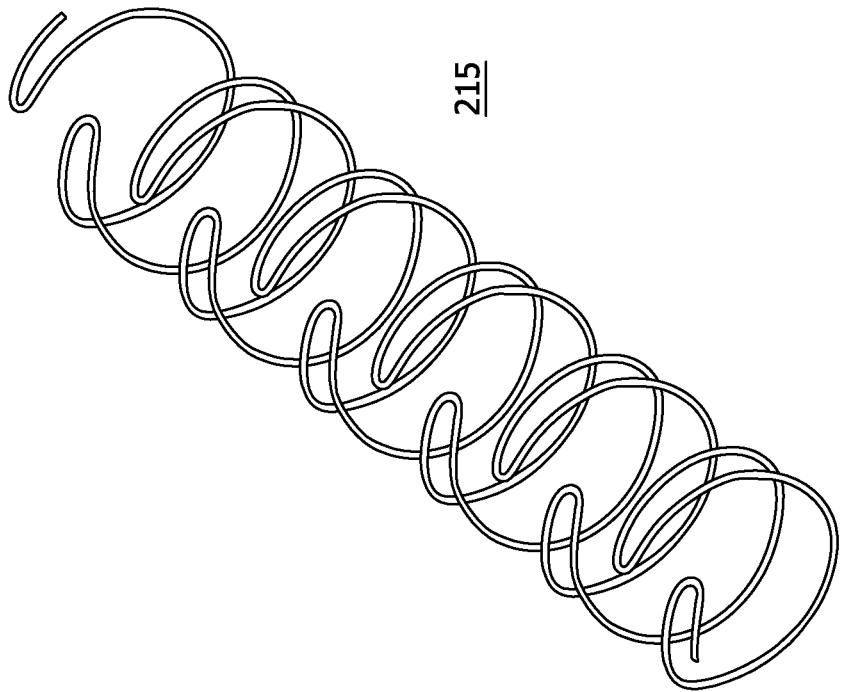
FIG. 2B illustrates a reinforcement member having a sinusoidal configuration in accordance with the present disclosure.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "proximal" and "distal," when used herein in relation to a device or device component, refer respectively, to directions closer to and farther away from the device's operator. However, since the present disclosure is not limited to peripheral or central approaches, the device should not be narrowly construed when using the terms proximal or distal since device features may be slightly altered relative to the anatomical features and the device position relative thereto.

As used herein, the term "elongate element" is generally any longitudinally extending structure with or without a lumen therethrough. Thus, elongate elements include but are not limited to introducer sheaths, introducers, sheaths, tubes with lumens (e.g., catheters), solid rods, hollow or solid wires (e.g., guidewires), hollow or solid stylets, metal tubes (e.g., hypotubes), polymer tubes, pull cords or tethers, fibers, filaments, threads, electrical conductors, radiopaque elements, radioactive elements and radiographic elements. Elongate elements can be any material and can have any cross-sectional shape including, but not limited to, profiles that are elliptical (e.g., circles, ellipses, and the like), non-elliptical (e.g., triangles, rectangles, squares, hexagons, trapezoids, pentagons, stars, and the like), or random. Moreover, the cross-section can vary in shape and/or size from end to end.

In accordance with some embodiments, an endoluminal device comprises a tubular member and a reinforcement member. While a tubular member and a reinforcement member will be generally described herein as separate and distinct elements, in illustrative embodiments discussed below, they can be one and the same element.

With reference now to FIG. 1, a tubular member 105 is generally any elongate element having at least one wall, generally opposite first and second ends, and a longitudinally extending lumen extending therethrough. A tubular member thereby comprises both luminal and abluminal surfaces. In various embodiments, a tubular member can be formed as a tube, formed into a tube from one or more sheets, wraps, or the like, or otherwise formed.

Tubular member 105, including any component of tubular member 105, can include various materials including, but not limited to polymers, such as fluoropolymers like an expanded polytetrafluoroethylene ("ePTFE"), expanded modified PTFE, expanded copolymers of PTFE, nylons, polycarbonates, polyethylenes, polypropylenes, polyurethanes and the like. Tubular member 105 can also comprise various elastomeric materials. Tubular member 105 can be permeable, semi-permeable or impermeable.

Figure 2A:
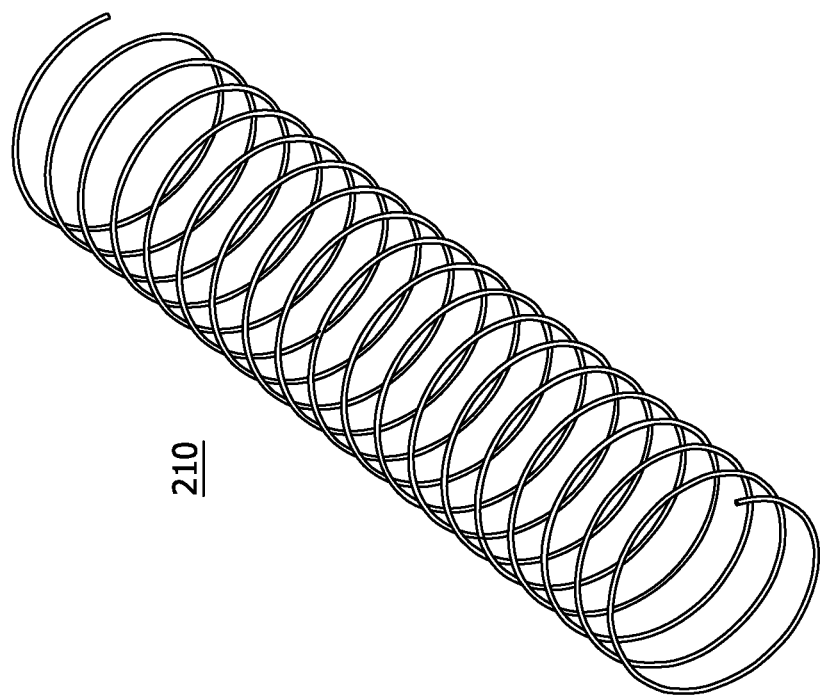
FIG. 2A illustrates a reinforcement member having a helical configuration in accordance with the present disclosure.

A reinforcement member is generally any elongate element configured to provide radial and/or longitudinal support to the tubular member and/or at least one wall of the tubular member. FIGS. 2A and 2B respectively depict illustrative embodiments comprising a helical reinforcement member 210 and a sinusoidal (e.g., zigzag, wavy or the like) reinforcement member 215. Notwithstanding those illustrative embodiments, a reinforcement member can generally be any continuous elongate element that provides radial support along substantially the entire length, or a portion of the entire length, of the tubular member and/or the wall of the tubular member. Such radial support is greater than about 180 degrees, or greater than about 270 degrees, or about 360 degrees.

The endoluminal device can include a single or a plurality of reinforcement members 210, 215 in series. In accordance with various embodiments, adjacent reinforcement members 210, 215 can be in series apex to apex or with offset apices. An individual reinforcement member 210, 215 can include a plurality of helical or sinusoidal sections, wherein each individual section is linear or has a sinusoidal configuration or the like. A helical reinforcement member 210 may be particularly useful in procedures not having a separate endoluminal device (e.g., a guidewire) extending through the tubular member. A sinusoidal reinforcement member 215 may be particularly useful in procedures having a separate endoluminal device (e.g., a guidewire) extending through the tubular member.

Reinforcement member 210, 215, including any component of reinforcement member 210, 215, can include a shape-memory material, such as nitinol. In other embodiments, however, reinforcement member 210, 215 can include other materials, self-expandable or otherwise expandable (e.g., with a fluid-filled balloon), such as various metals (e.g., stainless steel), alloys, polymers, expanded PTFE, Kevlar® and FEP.

In various embodiments, reinforcement member 210, 215 is a filament. The filament in turn can include, or otherwise be formed from one or more of expanded PTFE, Kevlar®, FEP, nitinol, stainless steel or other materials. In some embodiments, the filament has a generally round cross-section. In other embodiments, the filament has a generally flat cross-section. Put another way, reinforcement member 210, 215 having an axial to radial dimension ratio greater than 1 (e.g., being generally flat in the axial direction) can provide for a relatively smaller crossing profile for both its delivery and removal. Being generally flat in the axial direction can further provide for an increased surface area for contact with a surrounding tubular member.

Figures 3A, 3B:
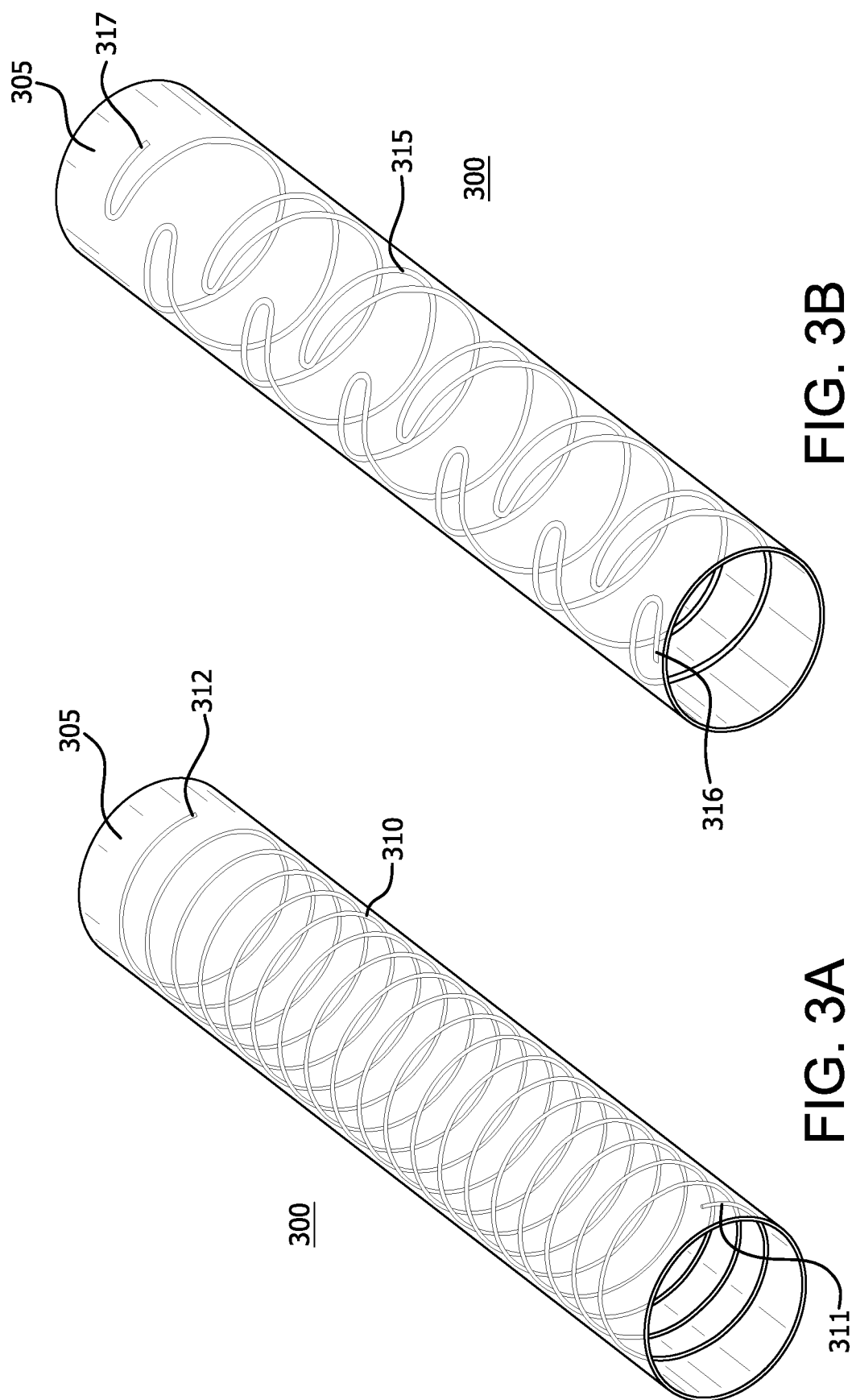
FIG. 3A illustrates an endoluminal device comprising a tubular member and a helical reinforcement member in accordance with the present disclosure.
FIG. 3B illustrates an endoluminal device comprising a tubular member and a sinusoidal reinforcement member in accordance with the present disclosure.

Turning now to FIGS. 3A and 3B, an endoluminal device 300 in illustrative embodiments comprises a tubular member 305 and a reinforcement member 310, 315. In some embodiments, reinforcement member 310, 315 is on an abluminal surface of tubular member 305, while in other embodiments, reinforcement member 310, 315 is on a luminal surface of tubular member 305. In still other embodiments, reinforcement member 310, 315 is sandwiched between a plurality of tubular members 305, or is disposed between a plurality of layers of a wall of tubular member 305.

In some embodiments reinforcement member 310, 315 is coupled to tubular member 305, or at least one wall of tubular member 305, by an adhesive such as FEP. In other embodiments, reinforcement member 310, 315 is sandwiched between a plurality of tubular members 305, or is disposed between a plurality of layers of a wall of tubular member 305. In general, any manner of coupling reinforcement member 310, 315 to one or more tubular members 305 is contemplated herein.

In accordance with illustrative embodiments, reinforcement member 310, 315 is removable in-situ. That is, a clinician can remove reinforcement member 310, 315 while the other components of an endoluminal device 300 remain in-situ. For example, the tubular member 305 can remain in-situ after removal of reinforcement member 310, 315, and can remain in-situ in a "wispy," "softer" or otherwise radially-unsupported or collapsible state that is more easily unattached from the vascular wall. Stated another way, in accordance with illustrative embodiments, the radial support exerted by reinforcement member 310 upon the luminal surface of the vascular wall can be removed along a portion of tubular member 305 such that it can be more easily unattached from the vascular wall.

Figure 4A:
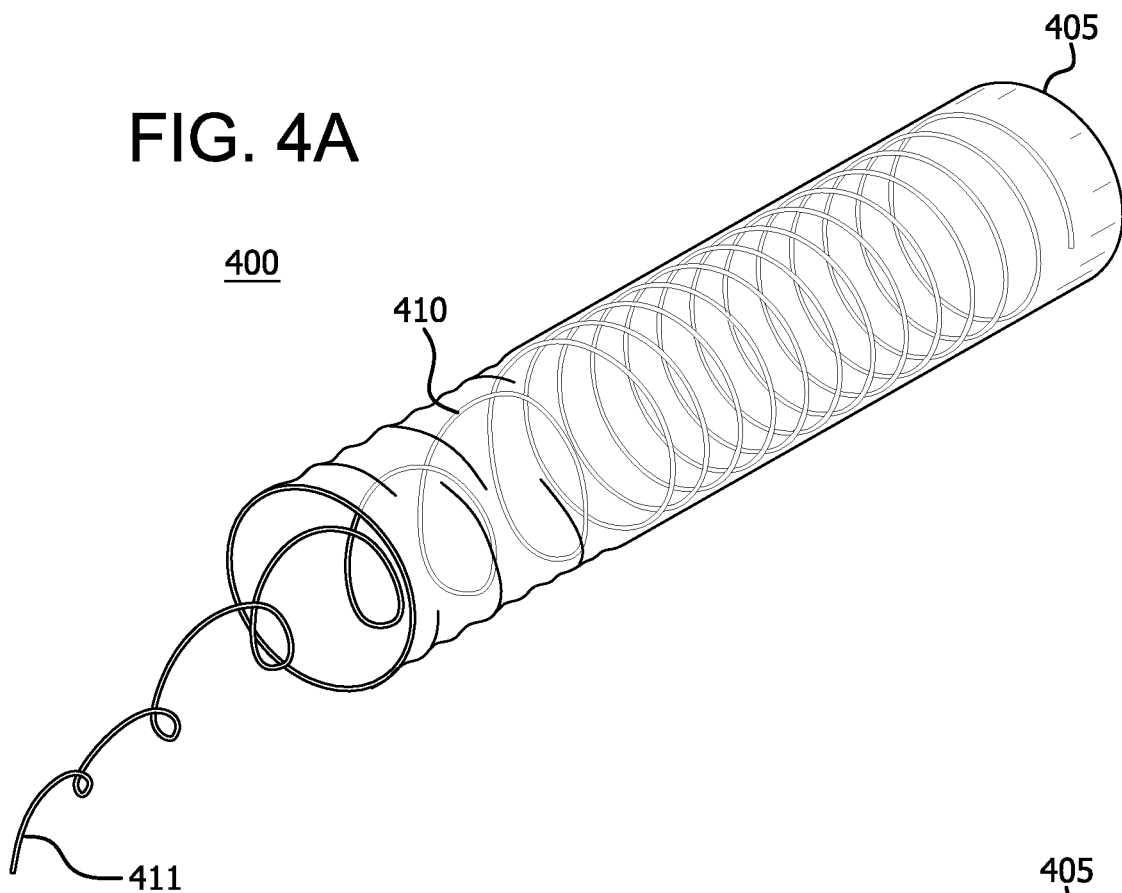
FIG. 4A illustrates an endoluminal device comprising a helical reinforcement member as deconstructable from a wall of a tubular member in accordance with the present disclosure.

By way of example, and with momentary reference to FIG. 4A, reinforcement member 410 is separable from a wall of tubular member 405 by applying a force to a proximal end 411 of reinforcement member 410. That is, by applying a force, such as an axial force or a rotational force, reinforcement member 410 can be torn through and/or otherwise removed from (e.g., "unscrewed" from) a wall of tubular member 405. In an illustrative embodiment, reinforcement member 410 is disposed between a plurality of layers of a wall of tubular member 405, and can be torn through one or more of the plurality of layers. In another illustrative embodiment, reinforcement member 410 is disposed between a plurality of layers of a wall of tubular member 405, and can be pulled from between, without tearing through, one or more of the plurality of layers.

Figure 4B:
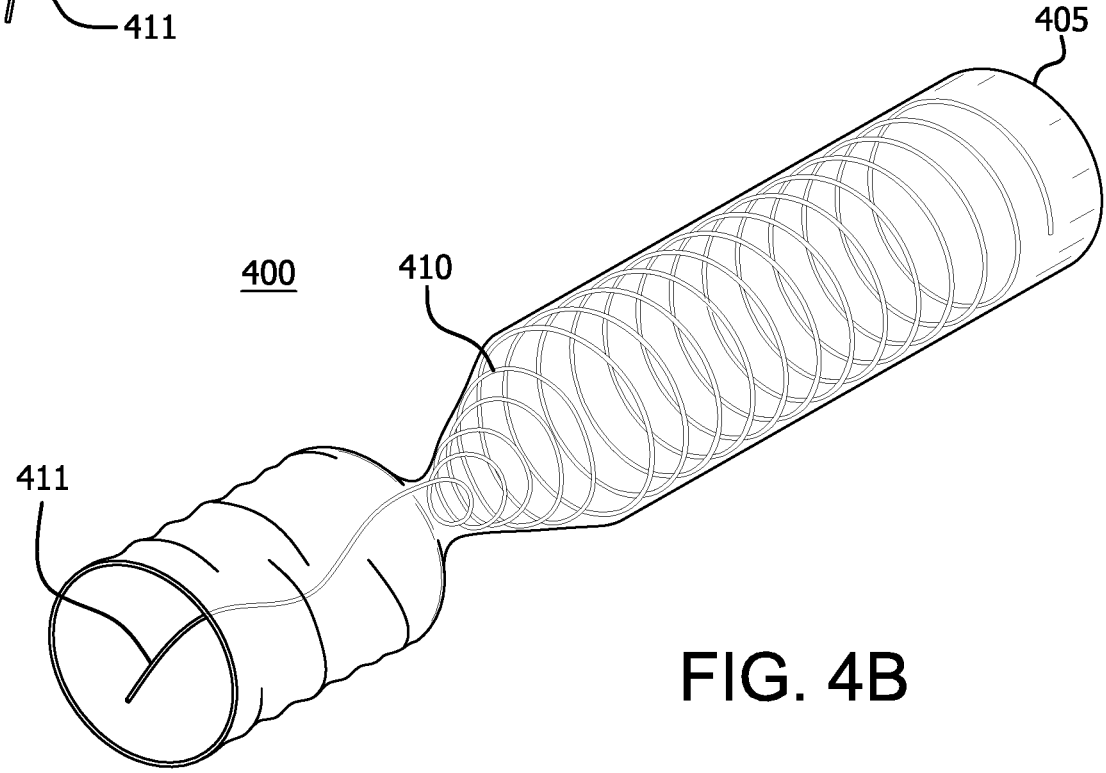
FIG. 4B illustrates an endoluminal device in accordance with the present disclosure, wherein the outer diameter of a wall of a tubular member is reduced temporarily.

In other embodiments, and with reference to FIG. 4B, by applying a force to a proximal end 411 of reinforcement member 410 to thereby remove reinforcement member 410 from tubular member 405, the outer diameter of a wall of tubular member 405 is reduced temporarily to break the seal between endoluminal device 400 and the host vessel, or otherwise detach endoluminal device 400 from the vascular wall.

Figure 4C:
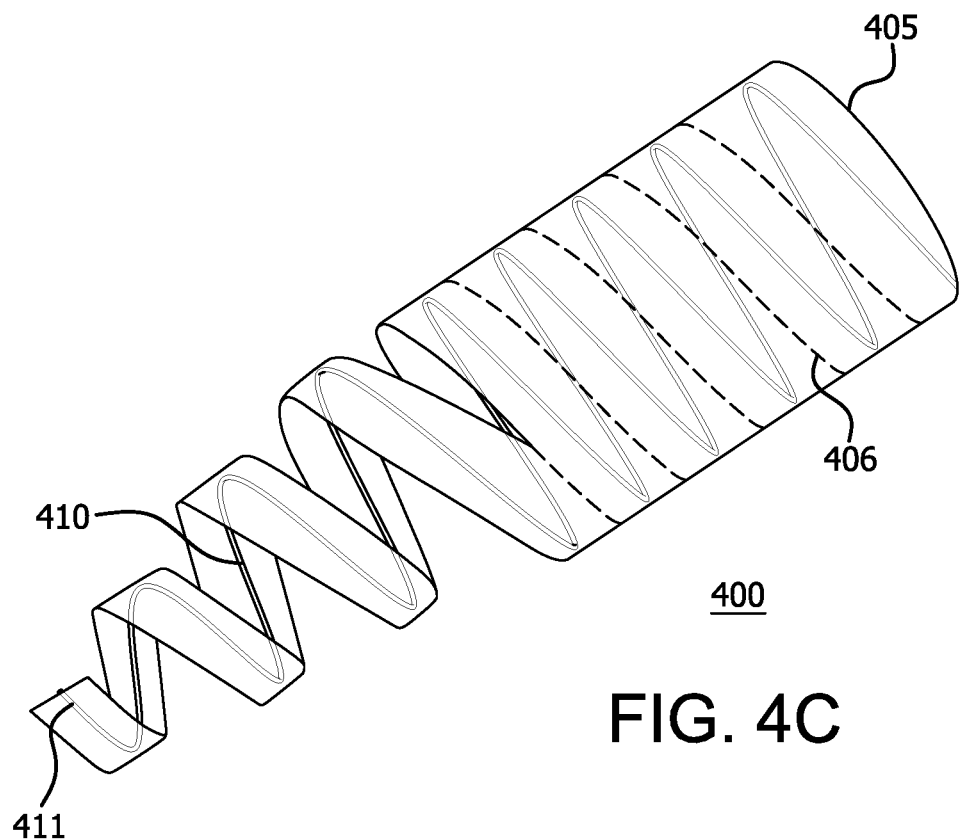
FIG. 4C illustrates an endoluminal device comprising a helical reinforcement member as deconstructable together with a wall of a tubular member in accordance with the present disclosure.

In yet other embodiments, and with reference to FIG. 4C, applying an axial force to proximal end 411 of reinforcement member 410 separates reinforcement member 410 together with a wall of tubular member 405. By way of non-limiting example, instead of tearing reinforcement member 410 through and/or otherwise from a wall of tubular member 405, the wall of tubular member 405 itself can be torn together with reinforcement member 410. Such embodiments can be facilitated by incorporating one or more perforations 406, for example, that coincide with the pattern of reinforcement member 410 between distal and proximal ends of tubular member 405. As used herein, the term "perforation" refers generally to a weakened portion, whether due to holes, scores or the like, or due to relative thickness, density, strength or the like of the subject material.

In illustrative embodiments, the one or more perforations 406 are offset from, yet in phase with, a pattern (e.g., helical or sinusoidal) exhibited by reinforcement member 410 so that opening the one or more perforations 406 does not decouple reinforcement member 410 from tubular member 405, or otherwise expose any portion of reinforcement member 410 to the subject's vasculature.

As alluded to above, in illustrative embodiments a tubular member and a reinforcement member can be one and the same element. In such embodiments, an endoluminal device 400 can be configured to radially and/or longitudinally support itself.

Figure 4D:
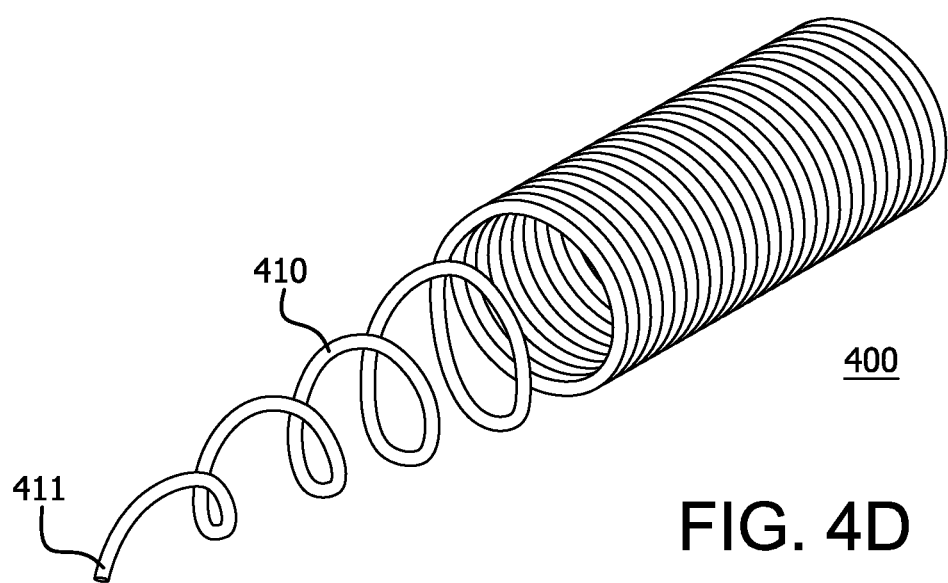
FIG. 4D illustrates an endoluminal device in accordance with the present disclosure, wherein a tubular member and a reinforcement member are the same element.

By way of example, and with reference to FIG. 4D, reinforcement member 410 can include a plurality of adjacent, helical windings that can be peeled from one another by applying a force to a proximal end 411 of reinforcement member 410. In such embodiments, the longitudinal strength of reinforcement member 410 is greater than the peel force necessary to peel a winding from an adjacent winding. In addition, reinforcement member 410 can have a shear strength sufficient to resist the shear forces associated with passing something through endoluminal device 400 (or passing endoluminal device 400 through the host vessel) such that adjacent windings would not come apart. In one such embodiment, ePTFE is coiled onto a mandrel so that adjacent windings are touching each other. Adjacent windings can be sintered together in an oven at from about 370 C to about 380 C for approximately 5 minutes. In other embodiments, an adhesive such as FEP can be used to couple adjacent windings.

Various materials other than ePTFE are also contemplated herein including, but not limited to polymers, such as fluoropolymers like PTFE, expanded modified PTFE, expanded copolymers of PTFE, nylons, polycarbonates, polyethylenes, polypropylenes, polyurethanes and the like. Moreover, it should be understood that, while the embodiment illustrated in FIG. 4D comprises a helical configuration, a sinusoidal configuration can also be used.

Turning back to FIGS. 3A and 3B, in other embodiments, applying an axial force to a distal end 312, 317 of reinforcement member 310, 315 deconstructs endoluminal device 300. In other embodiments, applying axial force to both a proximal end 311, 316 and a distal end 312, 317 of reinforcement member 310, 315 deconstructs endoluminal device 300.

In embodiments wherein deconstruction of endoluminal device 300 occurs in a distal to proximal fashion (i.e., an axial force is applied to a distal end 312, 317 of reinforcement member 310), such deconstruction can occur through the lumen of tubular member 305, that is, through the proximal end of tubular member 305. In an alternate embodiment, deconstruction of endoluminal device 300 can occur abluminally. Whether luminally or abluminally, reinforcement member 310, 315 can travel through a separate longitudinally extending structure comprising a lumen therethrough.

In illustrative embodiments, endoluminal device 300 is an introducer sheath for endoluminally delivering surgical implements to a treatment site. In other embodiments, endoluminal device 300 is an introducer, a sheath, or another elongate element (as that term has been described herein).

Figure 5:
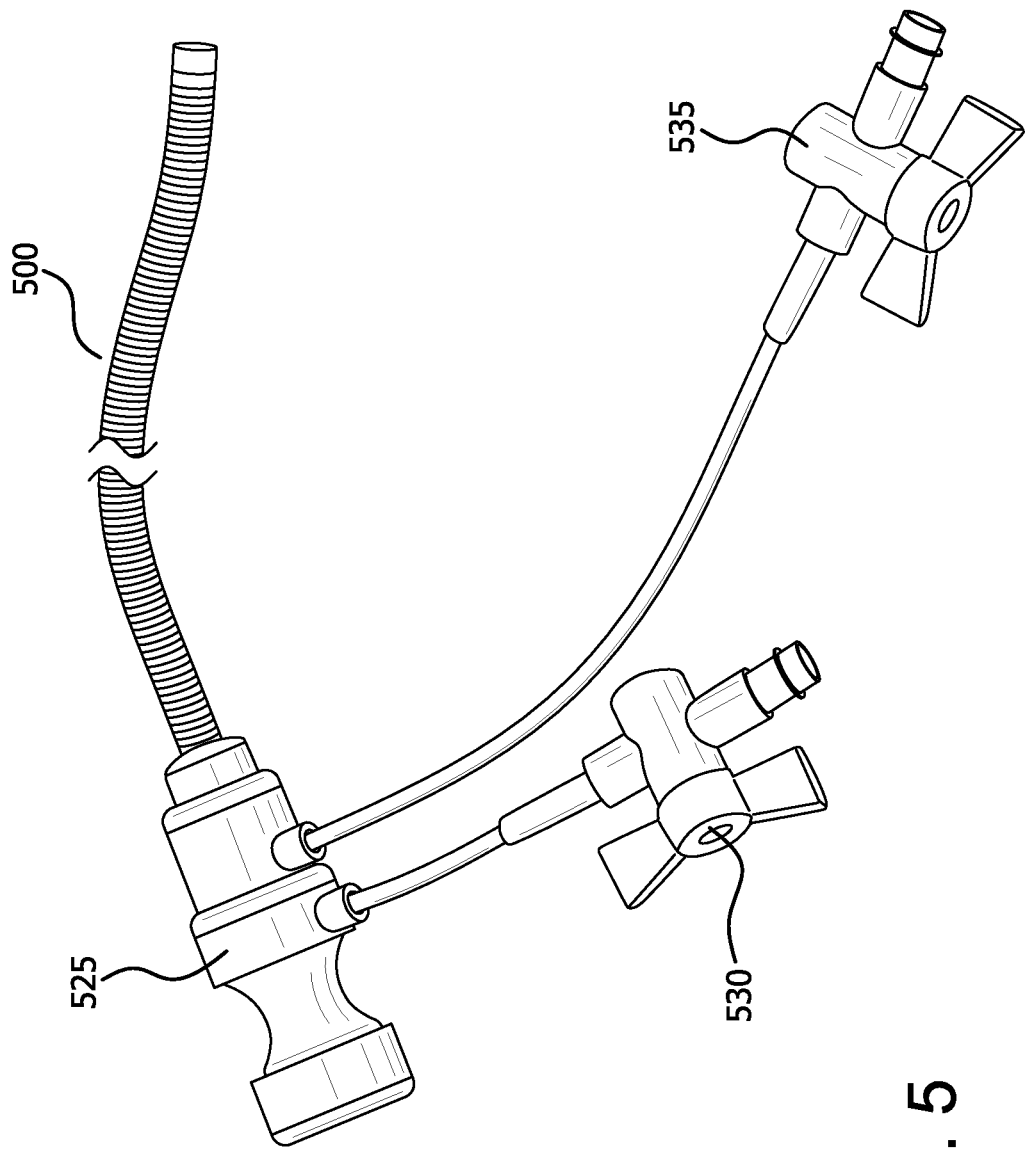
FIG. 5 illustrates a system in accordance with the present disclosure.

Systems are also disclosed herein. By way of example, and with reference to FIG. 5, in various embodiments a system 520 comprises an endoluminal device 500 as described herein coupled to a hub. The hub can in turn comprise one or more of a connector 525, a valve 530, a valve 535, a knob, a handle, and the like. In embodiments comprising a knob, an end of a reinforcement member of endoluminal device 500 can be attached to the knob, such that applying an axial force to the knob serves to deconstruct endoluminal device 500 as described supra.

In some embodiments, a knob is low-profile so as not to extend from the hub. In some embodiments, a knob comprises an indicator that it is to be used only in the event endoluminal device 500 has become attached to the vascular wall. Such an indicator can be an alpha-numeric indicator, a graphical indicator, or a combination of the foregoing.

Any portion of an endoluminal device as described herein can include elements which are passed through and/or attached at or near its proximal and/or distal end to facilitate or otherwise assist in the delivery and/or retrieval of the endoluminal device. Such elements can include one or more radio-opaque or echogenic elements, and/or surface elements or other mechanisms that facilitate coupling, for example, hooks, barbs, snares, loops, tethers, detents, or the like. Lubricous coatings can also be used to facilitate or otherwise assist in the delivery and/or retrieval of the endoluminal device.

Any portion of an endoluminal device as described herein can include a therapeutic agent, for example, be coated or imbibed with a therapeutic agent, whether dry, gel or liquid. Examples of therapeutic agents comprise antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)IIbIIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

In various embodiments, one or both of a therapeutic agent and a lubricous coating can be on a luminal surface of the tubular member and/or the reinforcement member. Similarly, one or both of a therapeutic agent and a lubricous coating can be on an abluminal surface of the tubular member and/or the reinforcement member. In some embodiments, the luminal and abluminal surfaces do not comprise the same therapeutic agent or lubricous coating.

Any portion of an endoluminal device as described herein can include a radio-opaque or echogenic element (e.g., markers or bands) that enhances imaging or detection during and/or following delivery or deployment. Such elements can include one or more of tungsten, gold, platinum and the like. Alternatively, standard radiopaque fillers (such as barium sulfate or bismuth subcarbonate) can be used to fill all, or one or more portions of an endoluminal device as described herein.

Methods of use are also disclosed herein. Upon completion of any vascular procedure where an endoluminal device as described herein remains in-situ for an extended period of time or is otherwise likely to become attached to the vascular wall, axial and rotational forces can be applied to the endoluminal device to determine whether it is attached to the vascular wall. If not attached to the vascular wall, the endoluminal device can be removed from the subject's vasculature without the need to deconstruct it as described herein. If, on the other hand, the endoluminal device is found to be attached to the vascular wall, an axial force can be applied to an end of a reinforcement member of the endoluminal device to separate it from a wall of a tubular member of the endoluminal device. Intermittently, during said separation, axial and rotational forces can be applied to the endoluminal device to determine whether it remains attached to the vascular wall. Once the endoluminal device is no longer attached to the vascular wall, it can safely be removed from the subject's vasculature.

An illustrative method thus comprises applying axial and rotational forces to an endoluminal device to determine whether it is attached to a vascular wall of a subject's vasculature; if the endoluminal device is determined to be attached to the vascular wall, applying an axial force to an end of a reinforcement member of the endoluminal device to separate it from a wall of a tubular member of the endoluminal device; intermittently, during said step of applying the axial force to the end of the reinforcement member of the endoluminal device, applying axial and rotational forces to the endoluminal device to determine whether it remains attached to the vascular wall; and removing the endoluminal device from the subject's vasculature once it is no longer attached to the vascular wall.

Example 1

Methods of making are also contemplated herein. In an embodiment, a tubular member comprised of an impermeable thin film ePTFE is laid up on an appropriately sized mandrel.

Next, a nitinol reinforcement member is placed over the tubular member. The nitinol reinforcement member is formed on an appropriately configured jig, either to have a helical or sinusoidal configuration. For a sinusoidal configuration, a flat sinusoidal pattern is rolled to assume a tubular sinusoidal configuration. In some embodiments, apices of the sinusoid are aligned upon rolling. In other embodiments, the sinusoid is rolled past 360 degrees, such that the apices are interleaved. The reinforcement member is heat set at approximately 450 C for approximately 20 minutes.

Optionally, the reinforcement member is powder coated with FEP, after which it is heat treated at approximately 320 C for approximately 2 minutes.

An overwrap of an impermeable thin film ePTFE is then applied, and the assembly is heat treated at approximately 320 C for approximately 15 minutes. The assembly is air cooled and removed from the mandrel.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An introducer sheath for endoluminally delivering surgical implements to a treatment site, said introducer sheath comprising:
a tubular member having generally opposite first and second ends, the tubular member defining a longitudinally extending central lumen, the tubular member having a wall and an elongated reinforcement member that extends between the first end and the second end along a profile of the wall along a non-linear path between the first end and the second end for reinforcing the wall the elongated reinforcement member being continuous and configured to provide radial support to the wall,
wherein the introducer sheath is removable in-situ via application of an axial force to at least one of the first end and the second end of the reinforcement member to tear the wall such that the wall is deconstructed as the reinforcement member together with torn portions of the wall are separated from a remainder of the wall.

2. An introducer sheath as set forth in claim 1, wherein the wall comprises expanded PTFE.

3. An introducer sheath as set forth in claim 2, wherein the wall includes a first layer and a second layer.

4. An introducer sheath as set forth in claim 3, wherein the wall includes a first layer and a second layer and the reinforcement member is disposed between the first layer and second layer of the wall.

5. An introducer sheath as set forth in claim 1, wherein the reinforcement member is a filament.

6. An introducer sheath as set forth in claim 5, wherein the filament is formed from at least one of expanded PTFE, Kevlar®, FEP, nitinol, and stainless steel.

7. An introducer sheath as set forth in claim 5, wherein the filament has a generally round cross section.

8. An introducer sheath as set forth in claim 5, wherein the filament has a generally flat cross section.

9. An introducer sheath as set forth in claim 1, wherein the reinforcement member extends along a sinusoidal pattern.

10. An introducer sheath as set forth in claim 1, wherein the reinforcement member extends along a helical pattern.

11. An introducer sheath as set forth in claim 1, wherein the wall includes a perforation extending parallel to the non-linear path of the reinforcement member.

12. An introducer sheath, said introducer sheath comprising:
- a tubular member comprising a wall,
- a reinforcement member disposed between a plurality of layers of the wall, the reinforcement member being continuous and configured to provide radial support to the wall, and
- a perforation through the wall that is offset from, yet in phase with, a pattern exhibited by the reinforcement member,
- wherein application of an axial force to an end of the reinforcement member causes the wall to be torn along the perforation.

13. An introducer sheath as set forth in claim 12, wherein the wall comprises expanded PTFE.

14. An introducer sheath as set forth in claim 12, wherein the reinforcement member is formed from at least one of expanded PTFE, Kevlar®, FEP, nitinol, and stainless steel.

15. An introducer sheath as set forth in claim 12, further comprising one of a therapeutic agent and a lubricous coating on a luminal surface of the tubular member.

16. An introducer sheath as set forth in claim 15, further comprising one of a therapeutic agent and a lubricous coating on an abluminal surface of the tubular member, wherein the luminal and abluminal surfaces do not comprise the same therapeutic agent or lubricous coating.

17. An introducer sheath as set forth in claim 12, wherein the reinforcement member extends along a sinusoidal pattern.

18. An introducer sheath as set forth in claim 12, wherein the reinforcement member extends along a helical pattern.

* * * * *